US008068892B2

(12) United States Patent
Russell (10) Patent No.: US 8,068,892 B2
(45) Date of Patent: Nov. 29, 2011

(54) METHODS AND SYSTEMS FOR USING INTRACRANIAL ELECTRODES

(75) Inventor: Michael J. Russell, Davis, CA (US)

(73) Assignee: Aaken Labs, Davis, CA (US)

( * ) Notice: Subject to any disclaimer, the term of this patent is extended or adjusted under 35 U.S.C. 154(b) by 574 days.

(21) Appl. No.: 12/139,443

(22) Filed: Jun. 13, 2008

(65) Prior Publication Data

US 2008/0312716 A1    Dec. 18, 2008

Related U.S. Application Data (63) Continuation-in-part of application No. 11/424,813, filed on Jun. 16, 2006.

(60) Provisional application No. 60/691,068, filed on Jun. 16, 2005.

(51) Int. Cl.
*A61B 5/04* (2006.01)

(52) U.S. Cl. .......................................... 600/378

(58) Field of Classification Search .................. 600/378; 604/174; 607/45, 116, 2, 48; 702/176; 439/39
See application file for complete search history.

(56) References Cited

U.S. PATENT DOCUMENTS

| | | | |
|---|---|---|---|
| 3,786,391 A * | 1/1974 | Mathauser | 439/39 |
| 3,865,099 A | 2/1975 | Robichaud | |
| 3,964,470 A | 6/1976 | Trombley | |
| 4,569,351 A | 2/1986 | Tang | |
| 5,701,895 A | 12/1997 | Prutchi et al. | |
| 5,995,651 A | 11/1999 | Gelenbe et al. | |
| 6,052,608 A | 4/2000 | Young et al. | |
| 6,319,241 B1 | 11/2001 | King et al. | |
| 6,662,035 B2 | 12/2003 | Sochor | |
| 6,795,737 B2 | 9/2004 | Gielen et al. | |
| 7,079,977 B2 * | 7/2006 | Osorio et al. | 702/176 |
| 7,107,104 B2 | 9/2006 | Keravel et al. | |
| 7,221,981 B2 | 5/2007 | Gliner | |
| 7,263,401 B2 | 8/2007 | Scott et al. | |
| 7,302,298 B2 | 11/2007 | Lowry et al. | |
| 7,346,382 B2 | 3/2008 | McIntyre et al. | |
| 7,620,456 B2 | 11/2009 | Gliner et al. | |
| 2005/0003268 A1 | 1/2005 | Scott et al. | |
| 2005/0075680 A1 * | 4/2005 | Lowry et al. | 607/45 |
| 2005/0131506 A1 | 6/2005 | Rezai et al. | |
| 2005/0177039 A1 | 8/2005 | Mills et al. | |

(Continued)

OTHER PUBLICATIONS

Sharan et al., "MR safety in patients with implanted deep brain stimulation systems (DBS)," *Acta Neurochir Suppl* (2003) 87:141-145.

*Primary Examiner* — George Manuel
*Assistant Examiner* — Robert N Wieland
(74) *Attorney, Agent, or Firm* — Morgan, Lewis & Bockius LLP; Jeffry S. Mann (57) ABSTRACT

The present invention relates to electrode assemblies, neurostimulation systems and methods for implanting and using same. In exemplary embodiments, the electrode includes a body having a conductive contact surface dimensioned and configured to contact a patient's skull; and an electrode head associated with the body. The electrode head is sized for subcutaneous positioning adjacent the subject's skull, and the electrode body is of a length and configured such that the electrode body extends at least partially through the patient's skull but does not contact the patient's dura mater. As these electrodes need not directly contact the brain nor penetrate the dura mater to be effective in neurostimulatory applications, they avoid many of the disadvantages, e.g. increased risk of infection and invasive implantation procedures, associated with conventional electrode design.

43 Claims, 5 Drawing Sheets

U.S. PATENT DOCUMENTS

| | | |
|---|---|---|
| 2005/0245984 A1 | 11/2005 | Singhal et al. |
| 2005/0246002 A1 | 11/2005 | Martinez |
| 2005/0283203 A1* | 12/2005 | Flaherty et al. ............ 607/48 |
| 2006/0129203 A1 | 6/2006 | Garabedian et al. |
| 2006/0173493 A1* | 8/2006 | Armstrong et al. ............ 607/2 |
| 2006/0173522 A1 | 8/2006 | Osorio |
| 2006/0241374 A1 | 10/2006 | George et al. |
| 2007/0106143 A1 | 5/2007 | Flaherty |
| 2007/0123954 A1 | 5/2007 | Gielen et al. |
| 2008/0300652 A1 | 12/2008 | Lim et al. |
| 2010/0036453 A1 | 2/2010 | Hulvershorn et al. |
| 2010/0113959 A1 | 5/2010 | Pascual-Leone et al. |

\* cited by examiner

METHODS AND SYSTEMS FOR USING INTRACRANIAL ELECTRODES

CROSS-REFERENCES TO OTHER APPLICATIONS

The present invention is a continuation-in-part of U.S. application Ser. No. 11/424,813, filed on Jun. 16, 2006, which application claims the benefit of U.S. application No. 60/691,068, filed Jun. 16, 2005, the contents of which are incorporated herein by reference in their entirety for all purposes.

FIELD OF THE INVENTION

The present invention relates generally to electrode assemblies, neurostimulation systems, and methods of neurostimulation using same.

BACKGROUND OF THE INVENTION

A wide variety of mental and physical processes are known to be controlled or influenced by neural activity in the central and peripheral nervous systems. For example, the neural functions in some areas of the brain (e.g., the sensory or motor cortices) are organized according to physical or cognitive functions. Several other areas of the brain also appear to have distinct functions in most individuals. In the majority of people, for example, the areas of the occipital lobes relate to vision, the regions of the left inferior frontal lobes relate to language, and the regions of the cerebral cortex appear to be involved with conscious awareness, memory, and intellect. Because of the location-specific functional organization of the brain, in which neurons at discrete locations are statistically likely to control particular mental or physical functions in normal individuals, stimulating neurons at selected locations of the central nervous system can be used to effectuate changes in cognitive and/or motor functions throughout the body.

In several existing applications, neural functions are tested, treated or augmented by electrical or magnetic stimulation powered by a neural stimulator that has a plurality of electrodes and a power source coupled to the electrodes. The electrodes can be implanted into the patient at a target site for stimulating the desired portions of the brain. For example, one existing technique for masking pain in a patient is to apply an electrical stimulus to a target stimulation site of the brain. In other applications, stimulation of an appropriate target site in the brain has shown promise for treating damage to and disease and disorders of the brain, including damage from strokes and treatment of Alzheimer's disease, depression, obsessive-compulsive behavior, and other disorders. In the surgical context, tcMEPs (transcranial stimulated electrical motor evoked potentials) have proven their advantages over wake-up tests in determining the integrity of the cortical spinal track during spinal and neurosurgical procedures.

The brain can be stimulated in several known fashions. One type of treatment is referred to as transcranial electrical stimulation (TES), which involves placing an electrode on the exterior of the patient's scalp and delivering an electrical current to the brain through the scalp and the skull. TES, however, is not widely used because the delivery of the electrical stimulation through the scalp and the skull causes patients a great amount of pain and the electrical field is difficult to direct or focus accurately due to shunting of electrical energy through the scalp.

Another type of treatment is transcranial magnetic stimulation (TMS), which involves using a high-powered magnetic field adjacent the exterior of the scalp over an area of the cortex. TMS does not cause the painful side effects of TES. Unfortunately, TMS is not presently effective for treating many patients because the existing delivery systems are not practical for applying stimulation over an adequate period of time. TMS systems, for example, are relatively complex and require stimulation treatments to be performed by a healthcare professional in a hospital or physician's office. The efficacy of TMS in longer-term therapies may be limited because it is difficult to (a) accurately localize the region of stimulation in a reproducible manner, (b) hold the device in the correct position over the cranium for the requisite period, and (c) provide stimulation for extended periods of time.

Another device for stimulating a region of the brain is disclosed by King in U.S. Pat. No. 5,713,922, the entirety of which is incorporated herein by reference. King discloses a device for cortical surface stimulation having electrodes mounted on a paddle that is implanted under the skull of the patient. These electrodes are placed in contact with the surface of the cortex to create "paresthesia," which is a vibrating or buzzing sensation. Implanting the paddle typically requires removal of a relatively large (e.g., thumbnail-sized or larger) window in the skull via a full craniotomy. Craniotomies are typically performed under general anesthesia and subject the patient to increased chances of infection due to the invasive nature of the procedure.

In view of the foregoing, there remains a need in the art for neurostimulation methods and electrodes that deliver electrical energy to the target site with minimized shunting and pain to the patient and that are implantable via less invasive and traumatic procedures.

SUMMARY OF THE INVENTION

The present invention relates to intracranial electrode assemblies, neurostimulation systems, and methods for implanting or using same. In exemplary embodiments, the electrode assembly includes a body having a conductive contact surface dimensioned and configured to electrically contact a patient's skull; and an electrode head associated with the shaft. The electrode head is sized for subcutaneous positioning adjacent the subject's skull, and the electrode is of a certain length and configured such that the electrode body extends at least partially through a patient's skull but does not contact the patient's dura mater. In some embodiments, the electrode has a distal end and is of sufficient length that, when implanted, the distal end rests within the inner cortical layer of the patient's skull. The electrodes provided herein avoid many of the disadvantages, e.g. increased risk of infection, invasive implantation procedures, associated with conventional electrode design as they, unlike their conventional counterparts, are not required to directly contact the brain, penetrate or even contact the dura mater to be effective in neurostimulatory applications. Those of skill in the art are aware of the tremendous difficulties in directing electrical energy through a patient's scalp or skull to an intended site in the brain. The TMS technique, while precluding a need for invasive craniotomies or implantation procedures, is reasonably directed. In addition to the shunting of electrical energy through the scalp, the electrical current must pass through the skull, which is known to possess a high resistivity. To ensure that the electrical stimulus reaches the brain, relatively high stimulus levels need to be employed to compensate for the effects of current spreading. The use of high stimulus levels, however, has the undesirable effect of stimulating large muscle groups and causing injuries, thereby limiting the duration of use and applications for this technology. Most distinctively, the present invention applies electrical stimulus directly to a site within a patient's skull. In some embodiments, the invention can be employed in conjunction with the methods described in the parent '813 application for modeling and predicting the path of current flow when electrical stimulus is first applied to a given site, e.g. in the skull, to achieve a more focused and directed neurostimulatory effect.

These and other objects, advantages, and features of the invention will become apparent to those persons skilled in the art upon reading the details of the invention as more fully described below.

BRIEF DESCRIPTION OF THE DRAWINGS

These and other advantages and features of the invention will become apparent upon reading the following detailed description and referring to the accompanying drawings in which like numbers refer to like parts throughout and in which.

| | |
|---|---|
| 10 | scalp |
| 20 | electrode assembly |
| 25 | neurostimulation system |
| 30 | electrode head |
| 40 | conductive shaft/electrode body |
| 50 | conductive contact surface |
| 60 | threads |
| 70 | lead |
| 75 | skull |
| 80 | outer cortical layer |
| 90 | cancellous bone |
| 100 | inner cortical layer |
| 110 | dura mater |
| 120 | conductive member |
| 130 | insulator/dielectric member |
| 135 | opening |
| 150 | connector |
| 160 | power source |
| 170 | fuse |

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the vector" includes reference to one or more vectors and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Overview

Various embodiments of the present invention provide electrodes and methods for implanting and using electrodes. It will be appreciated that several of the details set forth below are provided to describe the following embodiments in a manner sufficient to enable a person skilled in the art to make and use the disclosed embodiments. Several of the details and advantages described below, however, may not be necessary to practice certain embodiments of the invention. Additionally, the invention may also include additional embodiments that are not described in detail with respect to FIGS. 1-10.

Figure 1:
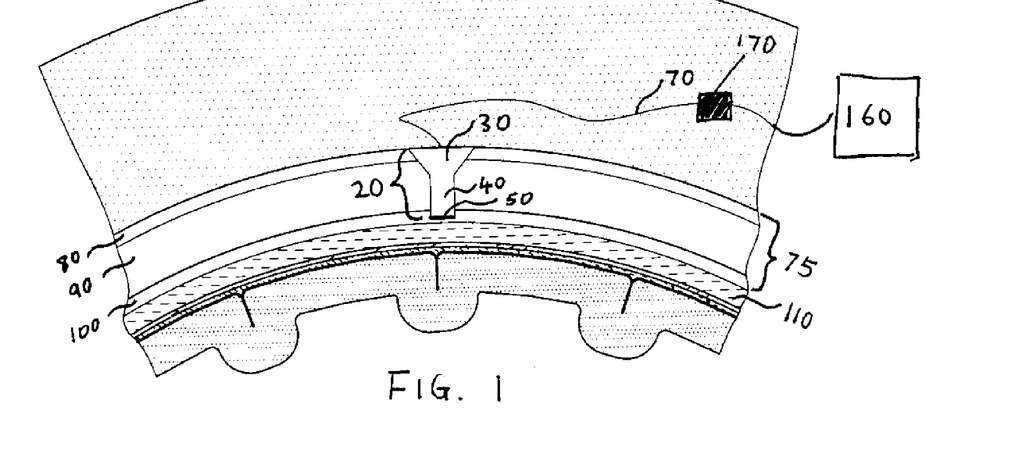
FIG. 1 is a schematic illustration of an electrode assembly in accordance with an exemplary embodiment of the invention implanted in a patient.
Figure 2:
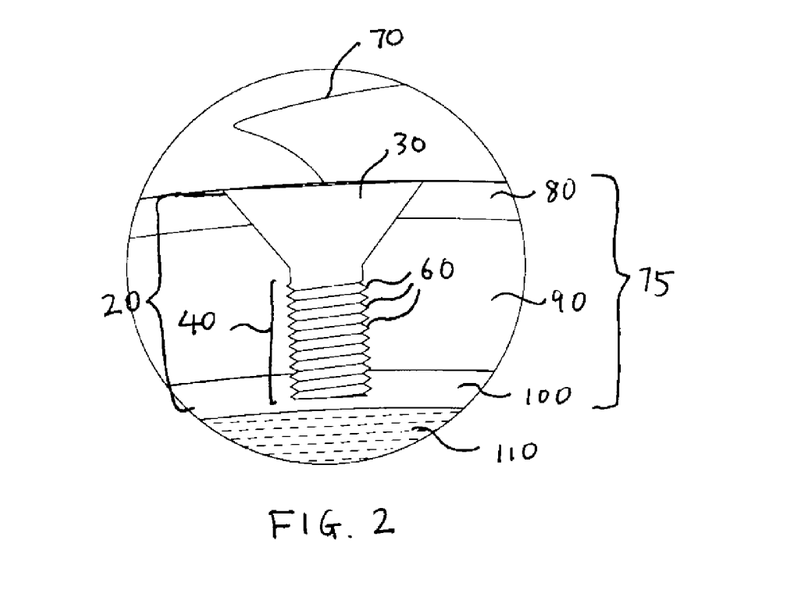
FIG. 2 is a schematic illustration of a threaded electrode assembly in accordance with an exemplary embodiment of the invention implanted in a patient.

In an exemplary embodiment of the invention, as illustrated in FIG. 1, an electrode assembly 20 having a body in the form of a shaft 40, to be inserted into a bore in a patient's skull, and an electrode head 30 is provided. The shaft includes a conductive contact surface 50 dimensioned and configured to apply electric or magnetic stimulation to a patient's skull 75. The electrode head 30 is associated with the shaft 40 and is sized to be positioned subcutaneously adjacent the patient's skull 75. This can ameliorate the difficulties associated with electrodes that protrude through the patient's scalp, including irritation of the skin and discomfort, and provide a more natural or cosmetically pleasing design for the implant patient. In an adaptation of the embodiment as shown in FIG. 2, the electrode structure includes threads 60 that are carried by at least one of the electrode head 30 and the shaft and may be dimensioned and configured to fix the electrode assembly 20 with respect to the patient's skull 75. In some embodiments, the electrode body 40 extends at least partially through the patient's skull 75, e.g. stopping at the outer cortical layer 80, cancellous bone 90, or inner cortical layer 100, but does not contact the patient's dura mater 110. As illustrated in FIG. 2, the electrode body 40 may be of a length sufficient for its distal end to rest within the inner cortical layer 100. In still further embodiments shown in FIGS. 1, 3 and 6, the conductive contact surface 50 is positioned on the body 40 so as to electrically contact at least one of the patient's skull tissues, namely the outer cortical bone 80, cancellous bone 90, or the inner cortical bone 100, when the electrode assembly 20 is in place. In some embodiments, the conductive contact surface 50 is positioned and configured to electrically contact the inner cortical layer 100 of the skull 75. As shown in FIG. 1, the conductive contact surface may be positioned distally on the electrode body.

Figure 8:
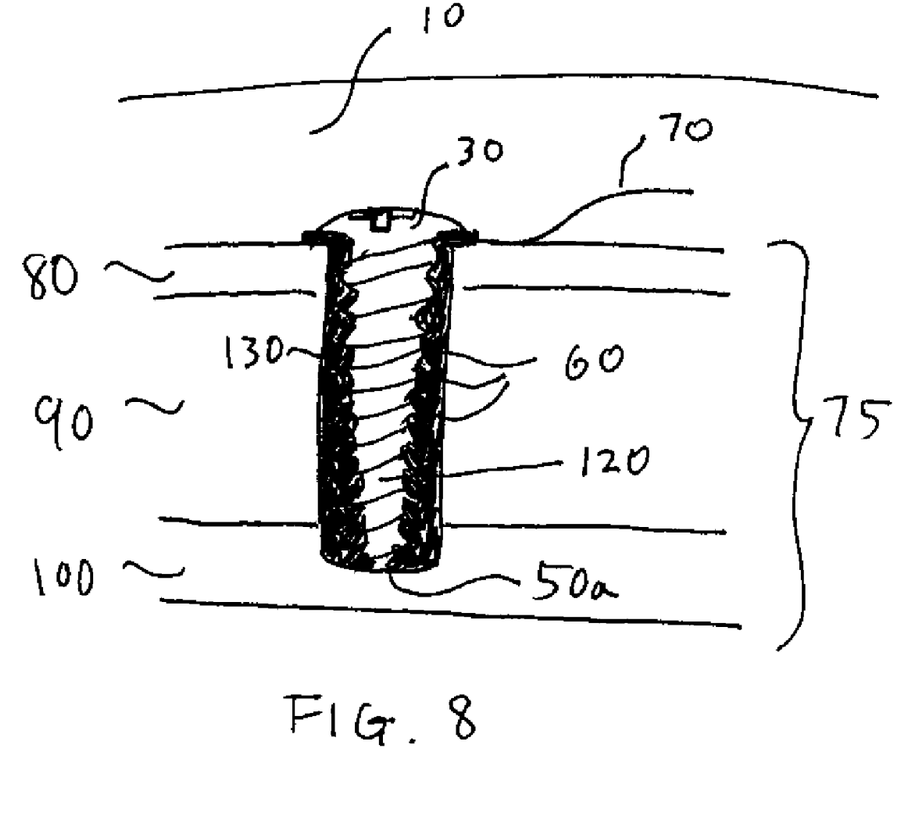
FIG. 8 is a schematic illustration of an electrode assembly with a tapered dielectric sleeve and a conductive member resting within in accordance with an exemplary embodiment of the invention implanted in a patient.

Another exemplary embodiment of the invention, shown in FIG. 8, provides an electrode that includes an electrically conductive member 120, a dielectric member 130, and an anchor. The electrically conductive member 120 has a blunt contact surface 50a and the dielectric member 130 has an interior in which the electrically conductive member 120 is received. One will appreciate that the dielectric member 130 may be applied to the electrically conductive member 120 to insulate as desired, e.g. areas other than the contact surface 50a. The anchor may be carried by the electrically conductive member 120 or the dielectric member 130. The anchor is dimensioned and configured to anchor at least one of the electrically conductive member 120 and the dielectric member 130 with respect to a patient's skull 75 such that the contact surface 50a of the electrically conductive member 120 is disposed against at least one of the patient's skull tissues, i.e. outer cortical bone 80, cancellous bone 90, inner cortical bone 100, and the dielectric member 130 electrically insulates the skull 75 from the electrically conductive member 120 except at the conductive contact surface 50a. In some embodiments of the invention shown in FIG. 9, the dielectric member 130 has an opening 135 through which the electrically conductive member 120 can protrude and contact the patient's skull tissue 75. As those of ordinary skill will appreciate, the assembly of the dielectric member 130 and electrically conductive member 120 can be removably or permanently secured using any mechanisms known in the art.

As readily appreciated by those of skill, the precise length of the electrode body 40 will vary depending on various factors, including without limitation the region of the skull selected for implantation and individual patient's skull thickness. However, the design of the present invention is such that the electrode body 40 extends at least partially through the patient's skull 75 but does not contact the patient's dura mater 110 when implanted.

For longer term applications, the electrode assembly 20 should be formed from a material of sufficient structural integrity to remain secured to the skull 75 for the duration of its intended use. For instance, the dielectric member 130 or the shaft 40 may be porous or textured to promote osseointegration of long-term implants. For shorter-term applications, the dielectric layer 130 and/or shaft 40 may be formed of or covered with a material that will limit osseointegration. In preferred embodiments, the electrode assembly 20 of the present invention is formed from a biocompatible material that is suitable for implantation purposes.

Exemplary conductive materials useful in the present invention include, without limitation, metal, carbon, ceramic, and/or conductive elastomers, etc. Conductive metal, if used, can be selected from platinum, stainless steel, silver, and/or gold, amongst other suitable metals. Elastomers may be made electrically conductive, e.g., by filling a polymeric material with a suitable quantity of a conductive metal powder or the like. In another embodiment, one or more wires may be embedded in the elastomeric material to conduct an electrical signal across the elastomer. In preferred embodiments, the conductive portion(s) are formed from a biocompatible material.

Exemplary dielectric materials useful in the present invention include, without limitation, electrically insulative ceramic and/or polymer. The dielectric polymer can be selected from any suitable material known in the art, such as silicone, polyamide, polyester, polytetrafluoroethylene, polyethylene, polypropylene, and hydrogel. In preferred embodiments, the dielectric portion(s) are formed from a biocompatible material.

Depending on the application, in some embodiments the electrode assembly 20 may be comprised of carbon and/or other non-ferrous materials so as to help minimize the formation of induced current in the presence of strong magnetic fields, e.g. from an MRI machine. Serious injuries, such as electrolytic lesions, have been documented to occur from MRI exposure with the generation of induced current in patients with ferrous implants. These instances may be avoided or reduced with the selection of a proper material for the electrode assembly 20 described herein.

Those of skill will also appreciate that the electrode assembly 20 of the present invention can be incorporated into the design of an electrode array (not shown). In some embodiments, the electrode array is implemented in the form of an electrode assembly 20 having multiple conductive contact surfaces 50. In alternative embodiments, the electrode array may comprise a plurality of electrode, each of which is connected to a separate electrical lead 70. Electrodes in the array may be identical or distinct. In applications where current distribution through a biological structure is desired, large conductive contact surfaces 50 (up to several square centimeters) may be preferred, as opposed to smaller conductive contact surfaces 50 (square millimeters or less) which would be more suited to situations where current focusing to a particular point is desired. As those of skill would appreciate, arcing may be avoided or minimized by using combinations of positive and negative currents.

Another exemplary embodiment of the invention provides a neurostimulation system 25. This neurostimulation system 25 includes an electrode assembly 20, a lead 70, a means 150 for operatively connecting the lead and the electrode, and a power source 160. The power source 160 may be a pulse system, constant current system, or others known in the art. The electrode assembly may take the form of any one of the preceding embodiments or a variation thereof. In one embodiment, the electrode includes a shaft including a distal contact surface dimensioned and configured to electrically contact a patient's skull tissue; an electrode head 30 associated with the shaft, with the electrode head 30 being sized to be positioned subcutaneously adjacent the patient's skull 75; and threads 60 carried by at least one of the electrode head 30 and the shaft 40, with the threads 60 being dimensioned and configured to fix the electrode with respect to the patient's skull 75. The lead 70 is dimensioned and configured to be subcutaneously implanted beneath the patient's scalp. The lead 70 has a first portion, which is dimensioned and configured to be electrically coupled to the contact surface 50, and an electrically insulated implantable length. The power source 160 may be selected to be a pulse system, a constant current system, or any other system known in the art, and is operatively coupled to the electrode assembly 20 via the lead 70 to apply an electrical stimulus to the skull tissue 75 and onto the brain via the electrode. As previously stated, a plurality of such electrodes may be employed in an array (not shown) and arranged in a configuration so as to generate an electrical potential between two or more electrodes in the array. In some embodiments as shown in FIG. 1, a fuse 170 or other overcurrent protective device known in the art is placed at a location along the circuit to prevent harm to the patient in the event of a circuit overload.

A method of implanting an electrode in accordance with another exemplary embodiment of the invention involves advancing an electrode through a patient's skull 75 until a contact surface 50 of the electrode body 40 is in contact with the patient's skull tissue 75, coming to rest at the outer cortical layer 80, cancellous layer 90, and/or the inner cortical layer 100. In some embodiments, the electrode head 30 and/or electrode body 40 is threaded. The electrode assembly 20 is electrically coupled to a lead 70. An electrode head 30 and the length of the lead 70 are covered with the patient's scalp 10, thereby enclosing the electrode and lowering the risk of infection. An electrical stimulus is applied to the patient's skull tissue 75 via the conductive contact surface 50, and allowed to travel to a predetermined site in the patient's brain. This electrical stimulus may be generated by a power source 160, e.g. pulse system, electrically coupled to the electrode by the lead 70.

Electrodes

FIGS. 1-10 illustrate electrodes in accordance with various embodiments of the invention.

Referring to FIG. 1, an electrode assembly in accordance with one exemplary embodiment of the invention is provided. This electrode assembly includes an electrode head 30 attached to a body 40 in the form of a shaft. In the illustrated embodiments, the body 40 is cylindrical, however, one will appreciate that other configurations may be used. For example, the body may have a triangular, square, rectangular or other suitable cross-section. The electrode head 30 and shaft 40 may be integrally formed. In some embodiments, both the electrode head 30 and shaft 40 comprise an electrically conductive material, e.g., titanium, or another biocompatible, electrically conductive metal. In some embodiments, the electrode head 30 may include one or more slots, an Allen electrode head recess, or other structure (e.g., a square drive or TORX™ drive recess) dimensioned and configured to facilitate advancing, rotating, or otherwise positioning the electrode. In select embodiments illustrated in FIGS. 4 and 5, wherein the electrode assembly 20 has a threaded shaft 40, as the electrode head 30 is turned, the threads 60 of the threaded shaft 40 will advance a generally distally positioned contact surface 50 of the electrode body 40 toward the dura mater 110. In embodiments where the electrode lacks threads as illustrated in FIG. 1, the electrode assembly 20 can be fixed in position using any means known in the art, e.g. bone cement. The length of the shaft 40 may be selected so that the contact surface 50 rests within the interior of a recess formed partially through a patient's skull 75 as to avoid contacting or piercing the dura mater 110 and the underlying cerebral cortex. The contact surface 50 may be relatively blunt and sized for insertion into the recess and configured to contact a predetermined point in the skull tissue 75 as selected in accordance with the methods detailed in the parent '813 application.

Figure 6:
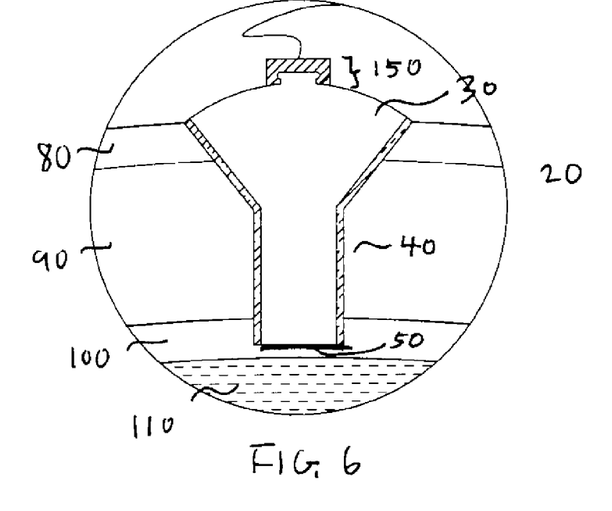
FIG. 6 is a schematic illustration of an electrode assembly with a snap mechanism for connecting the lead with the electrode head in accordance with an exemplary embodiment of the invention implanted in a patient.
Figure 7:
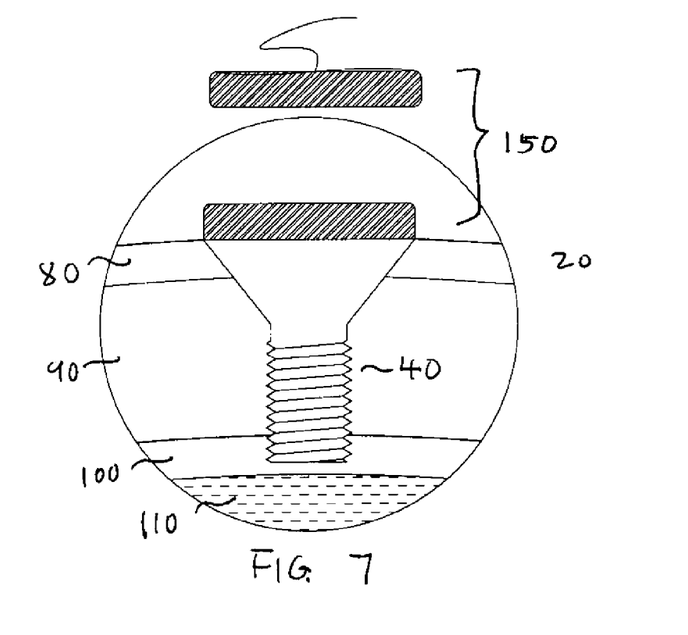
FIG. 7 is a schematic illustration of an electrode assembly with a magnetic coupling mechanism for connecting the lead with the electrode head in accordance with an exemplary embodiment of the invention implanted in a patient.

In some embodiments as illustrated in FIG. 1, the electrode assembly 20 is dimensioned and configured to be electrically connected to a power source 160 such as a pulse system, as described below. In an exemplary embodiment, the electrode assembly 20 is coupled to a power source 160 by means of an electrical lead 70. The electrical lead 70 may comprise an elongated, subcutaneously implantable body, which may have an insulating sheath. An electrically conductive ring or washer (not shown) may be attached to an end of the lead 70. In some embodiments, the lead 70 is physically attached to a component of the power source 160. In other embodiments, the lead 70 may be operatively connected to one or more components of the power source 160 without being physically attached thereto, e.g., using a transmitter and antenna or a magnetic coupling. Embodiments of systems incorporating such wireless links are disclosed in U.S. Patent Application Publication No. U.S. 2002/0087201, which is incorporated herein by reference in its entirety for all purposes. The lead 70 can be attached to the electrode using a connector 150 as shown in FIGS. 6 (snap illustration) and 7 (magnetic coupling illustration). The connector 150 may include a first component and a second component for releasably establishing a mechanical and electrical connection between the lead 70 and the electrode head 30. In exemplary embodiments, the connection between the lead and electrode can be made using pins, snaps, clamps, or via magnetic coupling.

Figure 3:
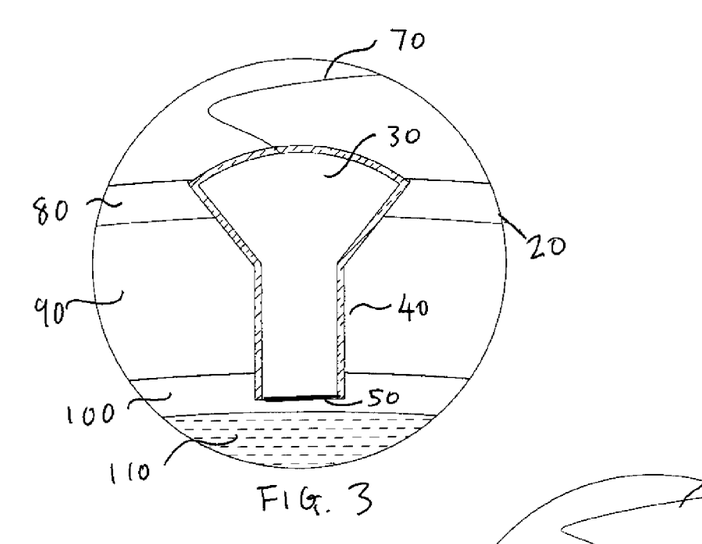
FIG. 3 is a schematic illustration of an electrode assembly with an insulation layer (indicated by diagonal hatching in all figures where present) in accordance with an exemplary embodiment of the invention implanted in a patient.

The electrode head 30 is dimensioned and configured to be implanted subcutaneously beneath the patient's scalp 10. The electrode assembly 20 may be used to apply an electrical stimulus to a site in the skull tissue 75 adjacent the contact surface 50, from where the stimulus will travel to a predetermined location in the brain along a path modeled with the guided electrical transcranial stimulation methods described in the parent '813 application. At higher stimulus levels, electrical contact between the patient's scalp 10 and the electrode head 30 may be uncomfortable or painful for the patient. If so desired, the scalp 10 may be electrically insulated from the electrode head 30 through any means known in the art. For example, this may be accomplished by coating the electrode head 30 with a quantity of dielectric, biocompatible, cementitious material, which may be cured or dried in place, as shown in FIG. 3. In other embodiments, the electrode head 30 is covered with a cap (not shown) formed of a dielectric material, e.g., a dielectric, biocompatible plastic, that may be glued, press-fit, or otherwise attached to the electrode head 30 and/or the lead 70.

Figure 4:
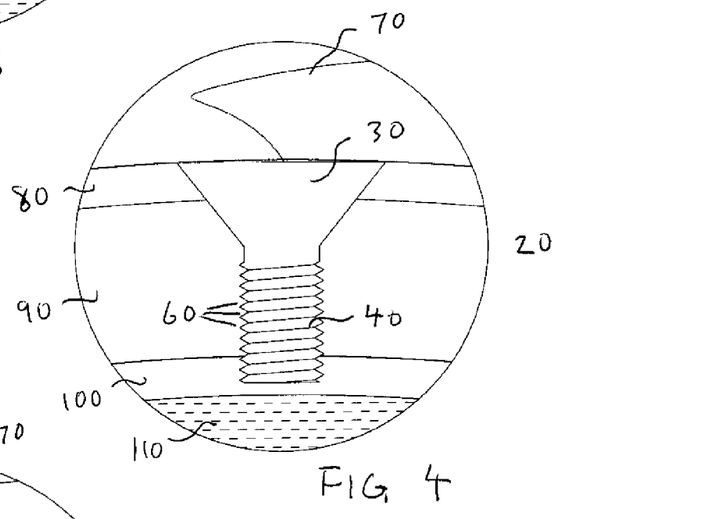
FIG. 4 is a schematic illustration of a threaded electrode assembly in accordance with an exemplary embodiment of the invention implanted in a patient.
Figure 5:
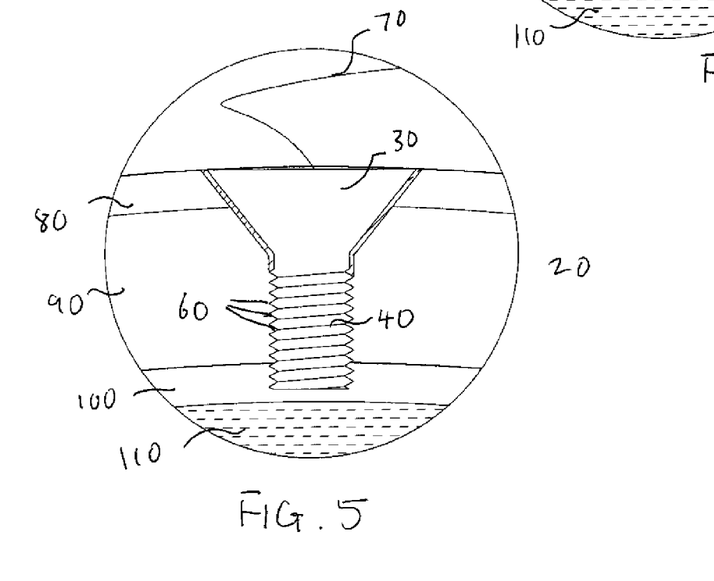
FIG. 5 is a schematic illustration of a threaded electrode assembly with a partially insulated head in accordance with an exemplary embodiment of the invention implanted in a patient.

The dimensions of the electrode assembly 20 can be varied to meet various design objectives. In various exemplary embodiments, the electrode body 40 is shorter than the depth of the patient's skull 75 at the site of insertion. More specifically, the electrode head 30 is dimensioned and configured to be seated at an extracranial subcutaneous site while the shaft 40 is only slightly shorter than the skull thickness at the site of implantation. Lengths selected for the electrode body 40 may vary, for example, the distal end of the electrode body 40 may be flush with the inner surface of the cranium. Alternatively, the electrode body 40 may be of a length that, when implanted, the distal end would rest somewhere within the outer cortical layer 80, within the cancellous layer 90, within the inner cortical layer 100, or spans two of the abovementioned layers. The diameter of the electrode head 30 and the electrode body 40 may also be varied. In some exemplary embodiments as illustrated in FIG. 3, the electrode body 40 is in the form of shaft and has a constant diameter throughout, but one will appreciate that the shaft diameter may vary. In alternative embodiments, the shaft 40 tapers distally to improve the ability of the shaft to be self-tapping. The electrode head 30 will often have a larger diameter than an adjoining portion of the shaft 40 as illustrated in FIGS. 3-5.

The electrode assembly 20 and the lead 70 can be connected using any means known in the art. In an exemplary embodiment, the electrode assembly 20 is electrically coupled to the lead 70 by compressively engaging the electrically conductive ring of the lead 70 between the electrode head 30 and a patient's skull. In some embodiments as illustrated in FIG. 8, the electrode includes an electrode head 30 having slots or other structure that can engage with a screwdriver, wrench, or the like. As previously described, the electrode head 30 can be dimensioned and configured to engage a cap (not shown) carried by the lead 70, wherein the cap serves to electrically couple the lead body 70 to the electrode head 30. In one example, the cap has a dielectric body (e.g., a dielectric plastic material with some resilience) with an electrically conductive interior. One manner of implementing the electrically conductive interior is to coat the interior surface of the cap with a conductive material. Preferably, the material employed is biocompatible and implantable for the purpose of the invention. The lead 70 may be coupled to the electrically conductive inner surface of the cap (not shown), thereby providing an electrical pathway between the electrode assembly 20 and a power source 160 operatively coupled to the lead 70. Where a cap (not shown) is used as a connector 150 between the electrode assembly 20 and the lead 70, the cap (not shown) may be dimensioned and configured to resiliently deform to be press-fitted on the electrode head 30.

In one exemplary embodiment, the cap (not shown) is sized to be subcutaneously implanted beneath the patient's scalp 10. For example, the electrode head 30 and the cap (not shown) may both extend outwardly beyond the outer cortex of the patient's skull 75. In another embodiment, some or all of the electrode head 30 and/or the cap (not shown) may be countersunk into a recess formed through the outer cortical layer 80 and/or an outer portion of the cancellous layer 90. This can improve patient comfort, which can be useful if the electrode is intended to be implanted permanently or for an extended period of time.

In alternative embodiments, the electrode assembly 20 may comprise an electrically conductive inner portion and an electrically insulative outer portion. The electrically conductive portion of the electrode includes an electrode head 30 and a body 40 defining a contact surface 50 for electrically contacting the interior of a bore formed partially through the patient's skull 75, into which the electrode assembly 20 is secured. In some embodiments, the shaft 40 is threaded. The electrically insulative outer portion of the electrode assembly 20 may include a dielectric member 130 disposed between the conductive member 120 and the patient's skull 75 as shown in FIG. 8. In one adaptation of this embodiment as shown in FIG. 8, the dielectric member 130 takes the form of a tapered sleeve. In some embodiments, the sleeve may have an upper ring-like portion and a plurality of deformable flanges extending distally therefrom. The flanges may be dimensioned and configured to be urged outwardly into compressive contact with a bore formed in the patient's skull 75 when the threaded conductive member 120 is advanced into the interior of the sleeve 130. To further secure the sleeve 130 in place with respect to the skull 75, ribs or teeth may be provided on the exterior surfaces of the flanges. In one embodiment, the sleeve is formed of a dielectric material, such as a dielectric polymer or ceramic, and the threads 60 of the threaded member may be self-tapping in the inner wall of the sleeve 130. The dielectric polymer can be selected from any suitable material known in the art, such as silicone, polyamide, polyester, polytetrafluoroethylene, polyethylene, polypropylene, and hydrogel.

Figure 10:
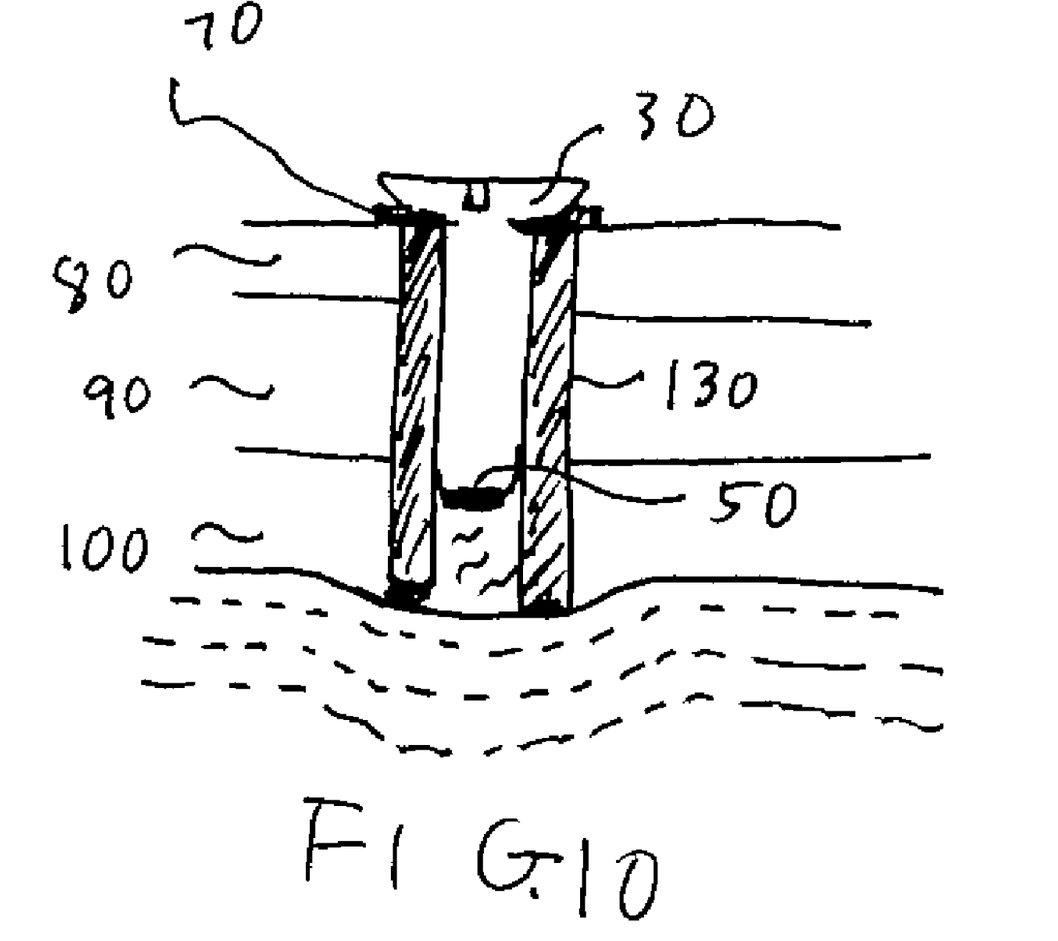
FIG. 10 is a schematic illustration of an electrode assembly having an electrode body extending partially through and within an insulator that extends through the skull and is dimensioned and configured to contact the dura mater.

In some embodiments as shown in FIG. 10, wherein the electrode assembly 20 comprises an electrode body 40 within an electrically insulative outer portion or insulator 130, the insulator 130 may extend through the skull 75 and is dimensioned and configured to contact the dura mater 110. The electrode body 40 extends partially through the insulator and has a length and configuration such that the electrode body 40 does not contact the patient's dura mater 110. The conductive contact surface 50 is positioned on the electrode body 40 within the insulator 130 such that the fluid (indicated by wavy lines) which would pool within the space defined by the electrode body 40, insulator 130, and dura mater 110 would conduct electricity from the contact surface 50 towards the dura mater 110. In certain embodiments, the electrode body 40 extends partially through the skull.

Figure 9:
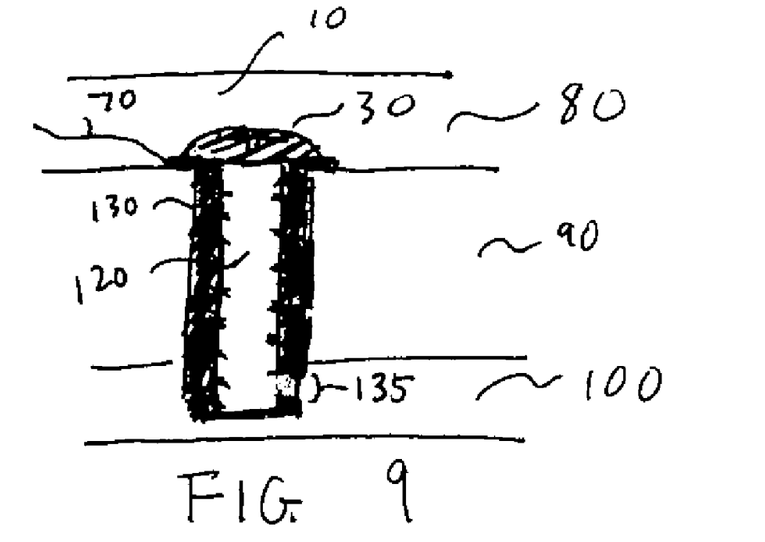
FIG. 9 is a schematic illustration of an electrode assembly with a dielectric sleeve having an opening through which the conductive member resting within can protrude in accordance with an exemplary embodiment of the invention implanted in a patient.

When implanted in a skull 75, the dielectric sleeve 130 will insulate part of the skull 75 from the electrically conductive member 120 of the electrode assembly 20. As an example, the dielectric sleeve 130 may insulate one or more of the outer cortical layer 80, cancellous layer 90, and inner cortical layer 100 from the conductive member 120. In a particular exemplary embodiment, both the outer cortical layer 80, cancellous layer 90, and a substantial portion of the inner cortical layer 100 are insulated from the conductive member 120 by the dielectric sleeve 130. The sleeve may have one or more openings through which the electrically conductive shaft can protrude and operably contact the skull at a preselected site as shown in FIG. 9.

As detailed in the present disclosure, some embodiments of the invention employ an array comprising a plurality of electrode assemblies 20 implanted at various locations in a patient's skull 75. The use of a dielectric member 130 such as the dielectric sleeve can help electrically isolate each of the electrode assemblies 20 from other units in the array and thereby prevent arcing. If so desired, a dielectric cap (not shown) can be used to insulate the patient's scalp from the electrically conductive electrode head 30 for all or some of the electrodes in an array and further minimize discomfort to the patient.

In still other exemplary embodiments, the electrode assembly 20 includes an electrically conductive member 120 electrically coupled to a subcutaneously implantable electrode head 30 and a distally positioned contact surface. The member 120 is received in the interior of an externally threaded dielectric member 130. In some embodiments, the shaft 40 is operatively coupled to the dielectric layer 130 for rotation therewith as the shaft 40 is advanced through the patient's skull 75. In one adaptation of this embodiment, this may be accomplished by a spline connection between the member 120 and the dielectric layer 130. In other embodiments, the dielectric layer 130 may be molded or otherwise formed about the conductive member 40 using any means known in the art.

As appreciated by those of ordinary skill in the art, the distance between the base of the electrode head 30 and the contact surface 50 may be fixed in some embodiments. However, as previously stated, the thickness of the skull 75 varies from patient to patient and from site to site on a given patient's skull. For increased adaptability, the electrode of the invention may have an electrically conductive shaft 40 that can selectively advanced or retracted with respect to the electrode head 30 such that the distance between the contact surface 50 on the shaft 40 and the electrode head 30 can be increased or decreased, respectively, and accommodate use at different depths of the skull 75.

In still other embodiments, the electrode head 30 comprises a body 40 and a tubular length that extends from the body 40. The body may be dimensioned and configured to be rotated by hand or by an installation tool. For example, the body 40 may have one or more recesses in its outer face sized and shaped to interface with a tool with projections dimensioned and configured to fit in the recesses, e.g. slotted, torx, hex, spannerhead, triple square, tri-wing, or any other configuration known in the art. In one adaptation of this embodiment, the tubular length is externally threaded so the electrode head 30 may be anchored to the skull 75 by screwing the tubular length into the skull 75. The shaft 40 may then move with respect to the skull 75 by rotating the shaft 40 with respect to the electrode head 30. In one adaptation of this embodiment, the electrode assembly 20 includes a shaft 40 that is slidably received by an electrode head 30.

For more precise control during the implantation process, the installation tool may also be a torque wrench or other tool dimensioned and configured to limit the amount of torque an operator may apply to the electrode head 30 during installation. Alternatively, the installation tool used may include graduations to indicate how far the shaft has been advanced with respect to the electrode head 30 and thereby facilitate control of the implantation process. Additional information such as the depth of the skull 75 at the site of implantation will further guide the implantation process.

In other embodiments, it is the shaft 40 rather than the electrode head 30 that is directly anchored into the skull 75. In such a configuration, the electrode head 30 may include an internally threaded bore that extends through the thickness of the electrode body 40 and the tubular length. The bore has threads sized to mate with the external threads 60 on the shaft 40. Rather than being threaded along its entire length, the shaft 40 may comprise of multiple portions, one or more of which are threaded. In these embodiments, the distance between the electrode head 30 and the contact surface 50 can be adjusted by rotating the shaft 40 with respect to the electrode head 30. To secure the shaft-head electrode assembly in place, the threads 60 in the distal portion of the shaft 40 can be designed to threadedly engage a distal portion of the threaded bore and the electrode head 30 is held in place by threadedly engaging with the threads 60 in the proximal portion of the shaft.

In one embodiment, the shaft 40 is threaded into a pilot hole in the skull 75. Once the shaft 40 is positioned to a desired depth, the electrode head 30 may be screwed onto a first proximal threaded portion of the shaft 40 to help fix the shaft 40 with respect to the skull 75 and provide a less traumatic surface to engage the patient's scalp 10 when the scalp 10 is closed over the electrode assembly 20. In another embodiment, the length of the electrode is first adjusted by rotating the shaft 40 with respect to the electrode head 30. Once the electrode has the desired length, the electrode assembly 20 can be implanted into the skull 75. To facilitate adjustment of the electrode length, the shaft 40 may be graduated as markers for the user.

To help prevent the penetration of fluids or infectious agents through the bore, a biocompatible seal, e.g., made of polytetrafluoroethylene or other suitable materials employed in the art, may be provided between the threads of the bore and the threads of the shaft 40.

In some embodiments, the electrode head 30 is formed of a dielectric material, such as a dielectric ceramic or dielectric polymer. The dielectric polymer can be selected from any suitable material known in the art, such as silicone, polyamide, polyester, polytetrafluoroethylene, polyethylene, polypropylene, and hydrogel. Use of a dielectric electrode head 30 can help electrically insulate the skull 75 from the electrode assembly 20 and respective units from each other when used in an array. In preferred embodiments, the dielectric material is biocompatible. As those of ordinary skill in the art will appreciate, in embodiments having a dielectric electrode head 30, the lead 70 and the shaft 40 will need be connected by a different configuration than those previously described, e.g. by electrically contacting the lead 70 to the proximal end of the shaft 40.

Referring to FIGS. 3 and 6, some or a substantial portion of the electrode head 30 extends outwardly beyond the outer surface of the skull 75. In alternative exemplary embodiments shown in FIGS. 4-5, the electrode head 30 can be configured so as to be received entirely within the skull, which configuration results in a more natural folding of the scalp 10 over the implantation site. However, those of ordinary skill in the art will appreciate that this is not necessary for the operation of the electrode assembly 20 or the neurostimulation system 25 disclosed herein.

Connection Between Electrode and Power Source

As previously mentioned, the electrode assembly 20 may be electrically coupled to a power source 160 by a lead 70. The lead 70 may include a cap (not shown) having an electrically conductive inner surface coupled to a lead body 70. As those of skill would appreciate, any means known in the art for electrically connecting the shaft 40 and the power source 160 can be used to achieve the purpose of the present invention.

Systems Employing Electrodes

In an exemplary embodiment of the invention, the neurostimulation system includes one or more electrodes and a power source 160. Any suitable system, including a pulse system and a constant current system, known in the art can be used. The pulse system may be an external unit or an internally implantable unit. Exemplary implantable pulse systems or generators are disclosed in U.S. Pat. Nos. 7,239,918, 6,760, 626, 5,476,485 etc., the contents of which are incorporated herein by reference in their entireties. The pulse system may be implanted in the body of the patient at a location remote from the electrode(s).

An exemplary pulse system suitable for use in the neurostimulation system generally includes a power supply, an integrated controller, a pulse generator, and a pulse transmitter. The power supply can be a primary battery, such as a rechargeable battery or other suitable device for storing electrical energy. In alternative embodiments, the power supply is an RF transducer or a magnetic transducer that receives broadcast energy emitted from an external power source and converts the broadcast energy into power for the electrical components of the pulse system.

In some embodiments, the controller includes a processor, a memory, and a computer readable medium. The controller can be a computer, and the computer readable medium comprise instructions for performing the requisite control functions, that when loaded into the memory of the computer, will be run by the processor. In alternative embodiments, the controller may include an integrated RF or magnetic controller that communicates with an external controller via an RF or magnetic link. In such a circumstance, many of the executable instructions may be resident in the external controller and the integrated portion of the controller may comprise a wireless communication system.

The controller is operatively coupled to and provides control signals to the pulse generator, which may include a plurality of channels that send appropriate electrical pulses to the pulse transmitter. The pulse generator may have N number of channels, with at least one channel associated with each of N electrodes being employed. The pulse generator sends appropriate electrical pulses to the pulse transmitter, which is coupled to a plurality of electrodes. Suitable components for the power supply, integrated controller, pulse generator, and pulse transmitter are readily known to persons skilled in the art.

Where an array (not shown) of electrodes is employed, the array may include two or more electrodes of similar or dissimilar design, as exemplified by the embodiments previously described. The precise shape, size, and location of the array and the number of electrodes in the array can be optimized to meet the requirements of any particular application. In some embodiments, each electrode, when used singly or in an array, is electrically coupled to the pulse system by means of a separate lead having an elongate, subcutaneously implantable body. Where an array of electrodes is employed, the elongate bodies of the leads can be combined into a single subcutaneously implantable cable or ribbon.

The electrodes of these arrays may be provided with electrical signals in a variety of different manners. In some circumstances, one electrode or a subset of the electrodes may have an electrical potential distinct from that of either another electrode or another subset of electrodes See U.S. Pat. No. 7,305,268, disclosing methods for optimizing the control of electrical pulses delivered to the electrodes in an array. The methods and apparatus disclosed therein may be used to automatically determine the configuration of therapy electrodes and/or the parameters for the stimulus to treat or otherwise effectuate a change in neural function of a patient.

As will be appreciated by those of ordinary skill in the art, the electrodes of the invention may be used to monitor electrical potentials in electroencephalography. A suitable electroencephalograph may incorporate a system similar to the neurostimulation system previously described, but a sensing unit may be used in place of the pulse system. Suitable components for such a sensing unit are known to those skilled in the art of electroencephalography.

Methods

Further provided by the present invention are methods for implanting an electrode and/or methods of installing a neurostimulation system including an implantable electrode. Implantation of conventional cortical electrodes typically requires a full craniotomy under general anesthesia to remove a relatively large bone flap from the skull 75. Craniotomies are usually performed under general anesthetic and subject the patient to increased chances of infection.

In accordance with one embodiment of the present invention, the diameter of the electrode shaft is sufficiently small, e.g. about 5 mm or less, to preclude the need for a full craniotomy or the use of general anesthesia. To prep for the implantation, a small pilot hole may be formed partially through the thickness of the patient's skull 75 near or at the site where electrical stimulus will be directly applied. In exemplary embodiments where the site of electrical stimulus is selected using the methods disclosed in the above-mentioned '813 application, tomographic data of the skull 75 from MRI, CT, or other types of images would be available and can be readily used to estimate the thickness of the skull 75 at the site where the pilot hole is to be formed and guide the prepping and implantation process. Any suitable tool known in the art, e.g. a hand drill, can be used to form a bore shallow enough to avoid extending through the entire skull 75. A stylus may be inserted into the pilot hole to confirm that it strikes skull tissue. The drill may then be used to deepen the pilot hole in small increments, checking with the stylus after each increment to detect when the hole reaches the desired depth of the skull 75. Implicit in the present disclosure, the depth of the bore may extend to the outer cortical layer 80, cancellous layer 90, or inner cortical layer 100.

As those of ordinary skill would appreciate, the location of the pilot hole will vary depending on the design and dimensions of the electrode used, including for example the mechanism and structure by which the electrode is secured to the skull 75, the location of the conductive surface on the electrode, and the site in the skull 75 at which electrical stimulus is to be directly applied such that the current will predictably distribute and travel to the predetermined stimulation site in the brain. Once the desired site in the skull 75 has been identified, the physician can bore the pilot hole to guide the conductive contact surface of the electrode into position. In one embodiment, the physician may use anatomical landmarks, e.g., cranial landmarks such as the bregma or the sagittal suture, to guide placement and orientation of the pilot hole. In another embodiment, a surgical navigation system may be employed to inform the physician during the procedure. Briefly, such systems may employ real-time imaging and/or proximity detection to guide a physician in placing the pilot hole and in placing the electrode in the pilot hole. In some systems, fiducials are positioned on the patient's scalp 10 or skull 75 prior to imaging and those fiducials are used as reference points in subsequent implantation. In other systems, real-time MRI or the like may be employed instead of or in conjunction with such fiducials. A number of suitable navigation systems are commercially available, such as the STEALTHSTATION TREON TGS sold by Medtronic Surgical Navigation Technologies of Louisville, Colo., U.S.

Once the pilot hole is formed, the threaded electrode can be advanced along the pilot hole until the contact surface electrically contacts a desired portion of the patient's skull tissue 75. In one embodiment, the length of the electrode is selected or adjusted to achieve the desired level of contact and the electrode will be advanced until a known relationship with the skull 75 is achieved. Once this contact is detected, the physician may advance the electrode a small distance to ensure reliable electrical contact over time. In alternative embodiments, wherein the electrode is not threaded, bone cement or other gap filters or structures known in the art may be used to hold the electrode in place with respect to the skull 75.

As noted above in some embodiments, the electrode is electrically coupled to a lead. The timing of this coupling may vary with the nature of the coupling. For a lead employing a contact ring or the like positioned below the electrode head 30, the lead may be coupled to the electrode before the electrode is introduced into the skull 75. In other embodiments, the lead may be coupled to the electrode after the electrode is properly positioned with respect to the selected site of the brain. The lead, or at least a length thereof, may be implanted subcutaneously in accordance with procedures known in the art. The patient's scalp may then be closed over the electrode head 30 so the electrode is completely enclosed. This can materially improve patient comfort compared to more convention systems wherein epilepsy monitoring electrodes or the like extend through the scalp to an extracorporeal connection.

Once the electrode is in place, an electrical stimulus may be delivered from a pulse system via the lead and the electrode, through the patient's skull tissue 75 and ultimately to a site in the patient's brain. In certain embodiments of the invention discussed previously, a plurality of electrodes may be implanted in an array in the patient's skull 75 and each of the electrodes may be coupled to the pulse system by an electrically separate lead. The precise nature of the stimulus delivered via the electrode(s) can be varied as desired depending on the site at which the conductive surface contacts the patient's skull 75, the resistance to current flow at that location or beyond, the type of diagnosis or condition to be treated. The type and frequency of stimulus may be adjusted with the help of electrical modeling described in the above-mentioned '813 application.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An electrode assembly for neurostimulation comprising:
   a body having a conductive contact surface dimensioned and configured to electrically contact a patient's skull; and
   an electrode head associated with the body, the electrode head being sized for subcutaneous positioning adjacent the patient's skull, said body having a length and configured such that the body extends at least partially through the patient's skull, wherein no conductive contact surface of the electrode assembly contacts the patient's dura mater.

2. The electrode assembly of claim 1, wherein the body extends only partially through the patient's skull.

3. The electrode assembly of claim 1, wherein the body has a plurality of conductive contact surfaces.

4. The electrode assembly of claim 1, wherein the body and the electrode head are integrally formed.

5. The electrode assembly of claim 1, further comprising threads dimensioned and configured to fix the electrode assembly with respect to the patient's skull.

6. The electrode assembly of claim 1, wherein the body further comprises insulation.

7. The electrode assembly of claim 6, wherein the insulation covers all but the conductive contact surface.

8. The electrode assembly of claim 7, wherein the conductive contact surface is located at the bottom of the body.

9. The electrode assembly of claim 1 being comprised of a biocompatible material.

10. The electrode assembly of claim 1, wherein the conductive contact surface is comprised of a material selected from the group consisting of cotton, fabric, gel, liquid, metal, carbon, ceramic, and conductive elastomer.

11. The electrode assembly of claim 10, wherein the material is selected from the group consisting of platinum, stainless steel, silver, silver chloride, and gold.

12. The electrode assembly of claim 1, wherein the electrode head is electrically conductive, further comprising a dielectric cap dimensioned and configured to cover the electrode head and electrically insulate a patient's scalp therefrom.

13. The electrode assembly of claim 12, wherein the dielectric cap is comprised of a material selected from a dielectric polymer or dielectric ceramic.

14. The electrode assembly of claim 13, wherein the dielectric polymer is selected from the group consisting of silicone, polyamide, polyester, polytetrafluoroethylene, polyethylene, polypropylene, and hydrogel.

15. The electrode assembly of claim 1, further comprising a lead electrically coupled to the contact surface and dimensioned and configured to carry an electrical signal to or from the contact surface.

16. The electrode assembly of claim 1, further comprising a lead electrically coupled to the contact surface and the electrode assembly dimensioned and configured to be subcutaneously implanted adjacent the patient's skull.

17. The electrode assembly of claim 1, further comprising a lead dimensioned and configured to be subcutaneously implanted beneath the patient's scalp and said lead having a first portion dimensioned and configured to be electrically coupled to the contact surface and an electrically insulated implantable length.

18. The electrode assembly of claim 1, further comprising a lead electrically coupled to the contact surface, the lead being dimensioned and configured for supercutaneous attachment to the body to deliver the electrical signal to or from the contact surface.

19. The electrode assembly of claim 1, wherein at least a portion of the electrode head is dimensioned and configured to be received in a bore in the patient's skull.

20. The electrode assembly of claim 19, wherein the electrode head is electrically conductive, the electrode assembly further comprising a dielectric cap dimensioned and configured to electrically insulate the patient's scalp from the electrode head.

21. The electrode assembly of claim 20, further comprising an electrical lead electrically coupled to the contact surface.

22. The electrode assembly of claim 1, wherein the electrode head comprises a magnetic material.

23. The electrode assembly of claim 22, further comprising an electrical lead.

24. A neurostimulation system comprising:
   an electrode assembly having a body having a conductive contact surface dimensioned and configured to electrically contact a patient's skull; and an electrode head associated with the body, the electrode head being sized for subcutaneous positioning adjacent the patient's skull and the body having a length and configured such that the body extends at least partially through the patient's skull, wherein no conductive contact surface of the electrode assembly contacts the patient's dura mater;

a lead dimensioned and configured to be subcutaneously implanted beneath the patient's scalp, the lead having a first portion dimensioned and configured to be electrically coupled to the electrode assembly and an electrically insulated implantable length;

a connector to operatively connect said lead to said electrode assembly, wherein said connector includes a first component and second component for releasably establishing a mechanical and electrical connection between the lead and the electrode assembly; and an energy source operatively coupled to the electrode assembly via the lead to deliver an electrical stimulus to the brain via the electrode assembly.

25. The neurostimulation system of claim 24, wherein the body extends only partially through the patient's skull.

26. The neurostimulation system of claim 24, wherein the energy source is a pulse system.

27. The neurostimulation system of claim 24, wherein the energy source is a constant current system.

28. The neurostimulation system of claim 24, wherein the lead is physically attached to the body and to the energy source.

29. The neurostimulation system of claim 24, wherein the lead is physically attached to the electrode assembly but indirectly electrically coupled to the pulse system.

30. The neurostimulation system of claim 24, wherein said first component comprises a pin and said second component releasably engages said first component.

31. The neurostimulation system of claim 30, wherein the pin is provided with a detent and the second component releasably engages the first component.

32. The neurostimulation system of claim 24, wherein said first component comprises a snap and said second component releasably engages said first component.

33. The neurostimulation system of claim 24, wherein said first component comprises a clamp and said second component releasably engages said first component.

34. The neurostimulation system of claim 24, wherein said first component and second component are magnetically releasable from one another.

35. A method of neurostimulation, comprising:
forming a recess at least partially through the skull, said recess having an interior;
inserting an electrode assembly into the recess, said electrode assembly comprising a body having a conductive contact surface dimensioned and configured for applying electrical energy to the recess interior; and an electrode head associated with the body, the electrode head being sized for subcutaneous positioning adjacent a patient's skull and the body having a length and configured such that the body extends at least partially through the patient's skull, wherein no conductive contact surface of the electrode assembly contacts the patient's dura mater;
electrically coupling the electrode to a lead;
covering the electrode head and a length of the lead with the patient's scalp, thereby enclosing the electrode; and
delivering an electrical stimulus to the patient's brain via the electrode assembly, the electrical stimulus being generated by an energy source electrically coupled to the electrode assembly by the lead.

36. The method of claim 35, wherein the body extends only partially through the patient's skull but does not contact the patient's dura mater.

37. The method of claim 35, wherein the body further comprises insulation.

38. The method of claim 37, wherein the insulation isolates the body from the dura mater.

39. The method of claim 35, where said conductive contact surface is in electrical contact with the recess interior.

40. The method of claim 35, wherein said body has a plurality of conductive contact surfaces.

41. An electrode assembly for neurostimulation comprising:
a body having a conductive contact surface dimensioned and configured to electrically contact a patient's skull; and
an electrode head associated with the body, the electrode head being sized for subcutaneous positioning adjacent the patient's skull, said body having a distal end and a length sufficient, when implanted, for the distal end to rest within the inner cortical layer of the patient's skull, wherein no conductive contact surface of the electrode assembly contacts the patient's dura matter.

42. An electrode assembly for neurostimulation comprising:
an insulator extending through the skull and dimensioned and configured to contact the dura mater;
a body extending partially through the insulator, said body having a conductive contact surface and having a length and configured such that the conductive contact surface does not contact the patient's dura mater; and
an electrode head associated with the body, the electrode head being sized for subcutaneous positioning adjacent the patient's skull.

43. The electrode assembly of claim 42, wherein said body extends partially through the skull.

* * * * *